US012640229B1

(12) United States Patent
Spindel

(10) Patent No.: US 12,640,229 B1
(45) Date of Patent: May 26, 2026

(54) METHODS AND SYSTEMS FOR LEVERAGING LINKS BETWEEN PHENOTYPIC AND GENOTYPIC DATA FOR PLANTS

(71) Applicant: Monsanto Technology LLC, Saint Louis, MO (US)

(72) Inventor: Jennifer E. Spindel, University City, MO (US)

(73) Assignee: MONSANTO TECHNOLOGY LLC, Saint Louis, MO (US)

(*) Notice: Subject to any disclaimer, the term of this patent is extended or adjusted under 35 U.S.C. 154(b) by 1156 days.

(21) Appl. No.: 17/587,567

(22) Filed: Jan. 28, 2022

Related U.S. Application Data

(60) Provisional application No. 63/144,830, filed on Feb. 2, 2021.

(51) Int. Cl.
| | | |
|---|---|---|
| *G16B 20/40* | (2019.01) | |
| *G16B 20/20* | (2019.01) | |
| *G16B 50/30* | (2019.01) | |

(52) U.S. Cl.
CPC ............. *G16B 20/40* (2019.02); *G16B 20/20* (2019.02); *G16B 50/30* (2019.02)

(58) Field of Classification Search
CPC ......... G16B 20/40; G16B 20/20; G16B 50/30
See application file for complete search history.

(56) References Cited

U.S. PATENT DOCUMENTS

| | | | |
|---|---|---|---|
| 8,916,749 B2 | 12/2014 | Brugiere | |
| 2013/0325355 A1* | 12/2013 | Geha ...................... | G16B 20/20 702/19 |

(Continued)

FOREIGN PATENT DOCUMENTS

WO      WO2022/039847 A1      2/2022

OTHER PUBLICATIONS

Dill, Alyssa et al., "The Arabidopsis F-Box Protein SLEEPY1 Targets Gibberellin Signaling Repressors for Gibberellin-Induced Degradation" The Plant Cell, (Jun. 2004) vol. 16, 1392-1405 (14 pages).

(Continued)

*Primary Examiner* — Larry D Riggs, II
*Assistant Examiner* — Emilie A Smith
(74) *Attorney, Agent, or Firm* — Harness, Dickey & Pierce, P.L.C.

(57) ABSTRACT

An example method for linking phenotypic data with genotypic data, to facilitate plant development, includes combining a phenotypic data structure and a genotypic data structure into a combined data structure and separating the combined data structure into multiple segment data structures, where each segment data structure includes data for a target phenotype and genotypic data for multiple plants. The method also includes, for each of the multiple segment data structures, generating a probability vector including a probability value for each of multiple genetic locations in sequences of the plants and appending each probability vector to the respective segment data structure and then combining the multiple segment data structures into an aggregate data structure, whereby the target phenotype is linked, by the probability vector, to the multiple plants.

16 Claims, 5 Drawing Sheets

(56)           References Cited

U.S. PATENT DOCUMENTS

2020/0291489 A1 *   9/2020  Baumgarten  ..........  G16B 20/00
2024/0000030 A1 *   1/2024  Jighly  .....................  A01H 1/04

OTHER PUBLICATIONS

Spindel, J. et al., "Genome-wide prediction models that incorporate de novo GWAS are a powerful new tool for tropical rice improvement" Official Journal of the Genetics Society, (2016) vol. 116, 395-408 (14 pages).
Spindel, J. et al., "Association mapping by aerial drone reveals 213 genetic associations for Sorghum bicolor biomass traits under drought" BMC Genomics, (2018) vol. 19:679 (18 pages).
Zhou, Shengen et al., "Manipulation of plant architecture and flowering time by down- regulation of the GRAS transcription factor SlGRAS26 in Solanum lycopersicum" Plant Science, (2018) vol. 271, 81-93 (13 pages).
Zhou, Xiang and Stephens, Matthew, "Genome-wide Efficient Mixed Model Analysis for Association Studies" Nat Genet. (Jan. 2013) vol. 44(7), 821-824 (9 pages).

* cited by examiner

METHODS AND SYSTEMS FOR LEVERAGING LINKS BETWEEN PHENOTYPIC AND GENOTYPIC DATA FOR PLANTS

CROSS-REFERENCE TO RELATED APPLICATION

This application claims the benefit of, and priority to, U.S. Provisional Application No. 63/144,830, filed on Feb. 2, 2021. The entire disclosure of the above application is incorporated herein by reference.

FIELD

The present disclosure generally relates to methods and systems for use in plant development and, in particular, to methods and systems for leveraging links between phenotypic and genotypic data associated with plants in connection with facilitating such plant development.

BACKGROUND

This section provides background information related to the present disclosure which is not necessarily prior art.

In plant breeding, modifications are made in plants, either through selection of parents and offspring (i.e., "conventional breeding") or through more direct genetic manipulation (e.g., use of transgenes, gene editing, etc.). And, when desirable improvements are achieved, a commercial quantity of the resulting plants is developed by planting seeds from selected plants and harvesting the resulting seeds over several generations. Throughout the process, numerous decisions are made as part of such selection, based on characteristics and/or traits of the plants being bred and, similarly, on characteristics and/or traits of progeny (which are not guaranteed to inherit or exhibit the desired traits of parents and/or ancestors of the progeny). Traditionally, as part of this selection process, phenotypic and genotypic data are compiled across generations for the plant populations.

DRAWINGS

The drawings described herein are for illustrative purposes only of selected embodiments, are not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. The description and specific examples included herein are intended for purposes of illustration only and are not intended to limit the scope of the present disclosure.

In connection with breeding and plant development, plants are modified to enhance the performance of plant trait characteristics, which may include, but are not limited to, height, stalk/root strength, resistance to pests and disease, flowering characteristics, specific leaf area, leaf angle, stress tolerance, water-use efficiency, seed mass, and fruit/grain production. Measurements on any and all of such characteristics may comprise phenotypic data for the plants. Separately, the genomes of plants are available to breeders through use of sequencing techniques, whereby the specific gene sequences of the plants are identifiable. Limited understanding, however, exists for linking the phenotypic data to the genotypic sequence data, especially for large volumes of data (e.g., on the order of hundreds of thousands to hundreds of millions of individuals, etc.). A genome-wide association study, or GWAS, is an established method that can identify the associations therebetween, from which it is understood that genetic variations in individuals may be correlated with variations in observable traits within a population.

Uniquely, the methods and systems herein enable and establish linking between the phenotypic data and the genotypic locations, through processing and separating the volumes of data into segments and analyzing the segments both individually and in aggregate. The aggregate analysis provides an improved understanding of the correlation between the phenotypic data and the genotypic location(s) impacting the phenotypic data (e.g., as defined by probability values, etc.), often for a volume of data, which is beyond what is possible, via individual analysis alone, and which provides an output that can be leveraged in a number of applications as described herein.

Figure 1:
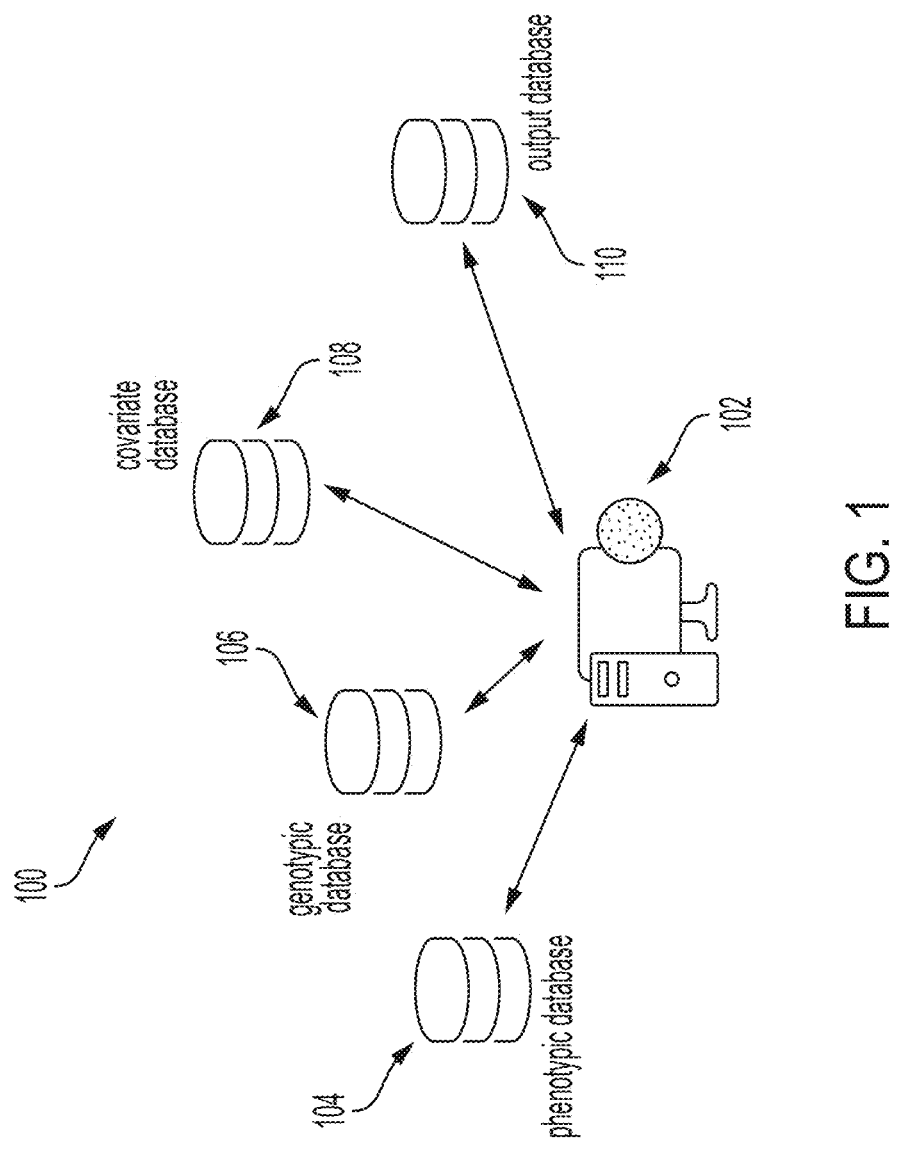
FIG. 1 illustrates an example system of the present disclosure suitable for linking phenotypic data from a data structure with genotypic data, through multiple probability values.

FIG. 1 illustrates an example system 100, in which one or more aspects of the present disclosure may be implemented. Although, in the described embodiment, parts of the system 100 are presented in one arrangement, other embodiments may include the same or different parts arranged otherwise depending, for example, on availability of data, location of data, relation of data to particular crops, relation of data to particular germplasm, etc.

As shown in FIG. 1, the system 100 generally includes a computing device 102, which is provided to link phenotypic data to genotypic data (including genotypic locations) through one or more probability values. The computing device 102 is coupled (as indicated by the arrowed lines in FIG. 1) in communication with multiple databases, including: database 104, which includes phenotypic data; database 106, which includes genotypic data; and database 108, which includes covariate data. In connection therewith, the computing device 102 is configured to access the data included in each of the databases 104, 106 and 108.

In this embodiment, the phenotypic database 104 generally includes quantitative and/or phenotypic data for millions of plants/breeding lines for a given crop (or for multiple given crops). In particular, one example crop includes corn (*Zea mays*). As such, in this example, the phenotypic database 104 may include, for example, a table (or tables) of traits for each maize line to pass through a breeding program including, but not limited to, flowering time measurements, grain yield, test weight, ear height, plant height, tassel traits, root lodging traits, stalk lodging traits, resistance to maize diseases and pests, kernels per row, rows per ear, and moisture, etc. In addition, the phenotypic database 104 may include various data associated with identification, description and/or location of the line(s), including, without limitation, geographic location (e.g., country, and sub-country locations, postal code, area code, etc.); types of growing spaces; fields, greenhouses, or other growing space location identities, etc.; germplasm identifiers (e.g., line codes, seed packet identifiers, unique database identifiers, etc.) pedigree information, data collection year, season, breeding pipeline, and breeding set identifiers, and maturity groupings; etc.

With reference again to corn or maize, an example entry of the phenotypic database 104 is illustrated in Table 1. This example is not limiting, but is provided to illustrate the types of data included for each of the plants/lines included in the database 104. As such, it should be appreciated that data included in the phenotypic database 104 may be consistent or inconsistent across different entries, especially with sources from different locations, regions or providers, etc.

species, orange, grapefruit, lemon, lime and other citrus, clover, linseed, olive, palm, *Capsicum, Piper*, and *Pimenta* peppers, sugarbeet, sunflower, sweetgum, tea, tobacco, and other fruit, vegetable, tuber, and root crops. The methods and systems herein may also be used in conjunction with non-crop species, e.g., model organisms such as *Arabidopsis thaliana*, etc. What's more, the methods and systems disclosed herein may be employed in various embodiments beyond plants, for example, for use in animal breeding programs, or other non-plant and/or non-crop breeding programs.

The genotypic database 106 in the system 100 generally includes genotypic data across thousands of individual plant accessions (e.g., plants/lines included in the phenotypic database 104, etc.).

For instance, the genotypic database 106 may include a table (or tables) comprising, but not limited to, plant line identification, the line's genomic DNA sequence, or more commonly an array of DNA genotypes at specific variable bases (hereafter referred to as genetic markers) and plant pedigree information (e.g., inbred, hybrid, crossing/family history etc.). Plant IDs included in the genotypic database 106 comprise a representation of the genetic history of a

TABLE 1

| Plant ID | Location | Field ID | Year | Plant Height | Ear Height | P50D | Yield | Test Weight | ... |
|---|---|---|---|---|---|---|---|---|---|
| $P_1$ | USA | 548778427063 | 2015 | 225 | 140 | 53 | 67 | 76 | ... |
| $P_2$ | USA | 548778427063 | 2016 | 220 | 110 | 55 | 60 | 74 | |
| $P_3$ | USA | 548778427063 | 2019 | 225 | 127 | 56 | 71 | 74 | |
| ... | ... | ... | ... | ... | ... | ... | ... | ... | ... |

It should be appreciated that additional plant traits (or characteristics) for crops beyond maize may include, but are not limited to, maturity time, heading date, fruit characteristics, fruit and seed size, quality traits/characteristics, resistance to crop specific diseases and pests, crop specific industrial processing requirements, specific leaf area, leaf angle, water use efficiency, stress tolerance, and agricultural crop standards. It should also be understood that the above quantitative plant trait data may be collected manually, or via gantry systems, ground-based vehicles (e.g., combines, etc.), and aerial drones, but are not limited to these collection methods.

It should also be appreciated that the phenotypic database 104 may be specific to, or inclusive of, other types of data related to other types of crops and/or plants and/or lines, including any fruits, vegetables, grasses, trees, or ornamental crops, including, but not limited to, soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including *indica* and *japonica* varieties); sorghum (*Sorghum bicolor*); sugar cane (*Saccharum* sp); tall fescue (*Festuca arundinacea*); turfgrass species (e.g., species: *Agrostis stolonifera, Poa pratensis, Stenotaphrum secundatum*, etc.); wheat (*Triticum aestivum*), and alfalfa (*Medicago sativa*), members of the genus *Brassica* (including broccoli, Brussels sprouts, cabbage, cauliflower, canola/rapeseed), carrot, Chinese cabbage, cucumber, dry bean, eggplant, fennel, garden beans, gourd, leek, lettuce, melon, okra, onion, pea, pepper, pumpkin, radish, spinach, squash, tomato, watermelon, honeydew melon, cantaloupe and other melons, banana, castorbean, coconut, coffee, cucumber, Poplar, Southern pine, *Radiata* pine, Douglas Fir, *Eucalyptus*, apple and other tree long-running commercial breeding program, and may represent all major morphology types in the organism of interest. The full database can also be altered by the researcher for specific experiments. Genomic DNA sequences, sets of genetic markers (a.k.a. haplotypes) and/or single genetic markers can be mapped for the purposes of GWAS using a variety of methods, including but not limited to, next-generation/Illumina based sequencing techniques, fixed arrays, or PacBio based sequencing. An example entry of the genotypic database 104 is illustrated in Table 2. This example is not limiting, but is provided to illustrate the genotypic data that may be included.

TABLE 2

| | Plant ID $P_1$ | Plant ID $P_2$ | Plant ID $P_3$ | ... |
|---|---|---|---|---|
| SNP1 | AA | TT | TT | ... |
| SNP2 | CT | TT | CC | ... |
| SNP3 | GG | CC | CC | ... |
| SNP4 | GG | GG | AA | ... |

The rows of the above table correspond to specific locations in the genomic sequence of the given individual where single nucleotide substitutions, known as single nucleotide polymorphisms (SNPs), are present in a large fraction of the population (e.g., ≥about 1-5% of the population, etc.), and the columns correspond to individual plant/line identifiers (e.g., Plant ID $P_x$, etc.). DNA nucleotides, then, are represented by one of four letters: adenine (A), thymine (T), guanine (G), and cytosine (C). Generally, there are two variants at each genomic location, and the sum of the variants across the genome represents the genetic variation of the population.

In general, it should be understood that the data structures 104 and 106 will also include at least some linking data, such as, for example, a plant ID, or genome ID, etc., upon which the different data in the data structures may be combined.

Further, the covariate database 108 in the system 100 includes, for example, variables known as covariates that are included in a genome-wide association study (GWAS) even though their effects on the phenotype of an organism are not of primary interest but should be included to rule out potential confounding variables (e.g., population structure, etc.). The covariate data generally includes, but is not limited to, possible combinations of principle components (PCs) calculated on the genetic data, and/or traits, treatments, time-points, and locations. The simplest covariate model, resulting in the QQ-plot with the least deviation from the null hypothesis, is selected herein to rule out false positives due to confounding.

It should be appreciated that the data structures 104, 106, and 108 may be cloud-based databases accessible via one or more network connections, or physical database(s), and which is/are coupled to the computing device 102, locally or via one or more networks, etc.

With that said, the computing device 102 is configured to access the databases 104 and 106 (and the database 108), and particular data therein. The data is pulled by species and program type, e.g., inbred corn, hybrid corn, hybrid canola, soybean, cotton, etc.

The computing device 102 may further be configured to perform quality control on both the phenotype database 104 and genotype database 106 (and the database 108) (or the data therein). For example, where the phenotype database 104 includes different units of measure (e.g., inches vs. cm, etc.) in various entries, the computing device 102 is configured to convert the data to a single unit of measure (e.g., all cm, or all inches, etc.). In another example, the computing device 102 may be configured to analyze the data for outlier entries in the database(s), through one or more known statistical techniques, etc. It should be appreciated that the computing device 102 may be configured to perform one or more further known techniques to ensure and/or improve the data from the databases 104, 106, and/or 108, for example (e.g., to account for human errors, differences in type of data collection, differences among regions associated with the collected data, etc.). Quality control measures on the databases are not necessarily limited to those described above, but at the minimum include those described here.

In this example embodiment, the computing device 102 is also configured to store the phenotypic data in a phenotypic data structure (e.g., object, container, etc.) in memory associated therewith (e.g., included in the computing device 102, or in the cloud, etc.), and to also store the genotypic data in a genotypic data structure in the memory (or in another memory associated with the computing device 102) (e.g., included in the computing device 102, or in the cloud, etc.). Alternatively, these structures could be stored in the same computing device along with one or more distinctions made between the two datatypes.

And then, the computing device 102 is configured to combine the data structures (in the memory(ies) or by cross-referencing of some kind) into a combined data structure, which includes both the phenotypic data and the genotypic data (e.g., Table 1 and Table 2 combined by the plant IDs, etc.). It should be appreciated that the data included in the combined data structure may be limited in one or more ways, for example, to affect processing times and/or based on data capabilities of the computing device 102, etc. For example, the combined data structure may be filtered to a subset of the phenotypic data (e.g., only plant height, etc.), or to those phenotypes that correspond to the genotypic data in the combined data structure. It may further be filtered on location, year, or other factors. The option of many different filters is present but some or all may or may not be applied in one or more, or every experimental case.

The computing device 102 is configured to then sort the data from the combined data structure into multiple segment data structures. In this example embodiment, the computing device 102 is configured to subset or compile the segment data structures from the combined data structure based on one or more factors, such as, for example, location and year, maturity group and year, or other relevant biological categories, etc. The factors may be selected based on one or more biological requirements, and to adjust the number of segment data structures and the number of individual lines within each segment data structure with regard to statistical power of the association test (e.g., to impact the confidence in the output below, etc.), etc. For example, phenotype entries may be filtered (or sub-setted) by year (e.g., 2015, 2016, 2017, etc.) and then further filtered (or sub-setted) by location (e.g., within a country or sub-country location, and/or by the use of internal sub-country location statistical clustering methods; etc.). Other options of filtering are also possible. The factors used for filtering (or sub-setting) may each be defined as (or referred to as) a macro-environment, where each resulting segment data structure is specific to one of the macro-environments. It should be appreciated that, like above, the sub-setting of the combined data structure can result in the omission of certain data and/or additional data filtering, and that the segments are run on specific phenotypic characteristics (e.g., height, etc.).

Additionally, within each of the segment data structures, the computing device 102 may be configured to combine entries for plants included in the given segment data structure to ensure one entry per plant within a given data structure (as defined, for example, by unique plant germplasm IDs, genome IDs, sequences, etc.). For multiple entries, then, the data included for the entries may be an average of the data included in the separate entries to provide the data for the consolidated entry in the data structure. For example, for five entries related to plant ID 123456, the computing device 102 may be configured to average the heights of the five entries (e.g., 295 cm, 324 cm, 290 cm, 312 cm, and 337 cm provides an average of 311.6 cm; etc.) to provide the height of the consolidated entry for plant ID 123456 in the segment data structure. Other methods besides averages may also be employed in this step to consolidate data on multiple lines.

Thereafter, in this example embodiment, for each of the segment data structures, the computing device 102 is configured to calculate a probability vector, which consists of a probability value (p-value) for each genetic marker (or genetic location of a SNP or other division of the plant genome sequence) that reflects the probability that the given variant (marker) is associated with an impact (e.g., a significant difference, etc.) in the one or more phenotypes of the lines that carry that variant. For example, for the phenotypic characteristic of height, the computing device 102 may be configured to determine, for each genetic marker (or genetic location or SNP) in the genotype structure, the probability that each marker variant is associated with a difference in the heights of individuals in the segment data structure. The computing device 102 may be configured, for example, to employ genome-wide efficient mixed-model association (GEMMA) to determine the probability values (see, Zhou, X., & Stephens, M. (2012): Genome-wide efficient mixed-model analysis for association studies, Nature genetics, 44(7), 821-824; and Spindel, J. E., Begum, H., Akdemir, D., Collard, B., Redona, E., Jannink, J. L., & McCouch, S. (2016): Genome-wide prediction models that incorporate de novo GWAS are a powerful new tool for tropical rice improvement, Heredity, 116, 395-408).

Specifically, the univariate linear mixed model as implemented in GEMMA may be utilized, in this example, to calculate the p-values for each genetic marker (or genetic location or SNP) in the genotype structure of the segment data structure (and for each segment data structure) and then append the p-value to the segment data structure. That said, it should be understood that other examples or implementations of the model may also be used in other embodiments, including, but not limited to, multivariate models, nonlinear models, and/or linear or non-linear models that capture GxG (gene-by-gene) and GxE (gene-by-environment) interactions, etc.

In this example embodiment, the computing device 102 is configured to then combine the segment data structures into an aggregate data structure, which includes the phenotypic data and the genotypic data (or subsets thereof) and the p-values calculated for those input segment data structures. The p-values are concatenated in the aggregate data structure, and further sorted by genetic marker (or genetic location or SNP). And, then, the computing device 102 is configured to store the aggregate data structure, as one potential output of the system 100, in an output database 110 (e.g., in an object or container, etc.), which may be either local, or not, and which may be in physical memory and/or in a cloud-based memory.

The computing device 102 is configured to then process the aggregate data structure, hereafter referred to as the aggregate data object, and to generate a result that may be leveraged to make breeding, editing, transgene insertion, or other biotechnological decisions. The methods included in the data structure are described below.

In connection therewith, however, the computing device 102 may be configured to first provide for error correction in the p-values. For instance, each individual test creates its own probability and therefore accepts or rejects the null hypothesis. For example, if the p-value falls below a predefined alpha value of 0.05, then 5% of the time, the null hypothesis is rejected when it is actually true and a false positive is detected. For GWAS applications, for example, the number of tests is often higher and creates a greater number of false positives (e.g. 100,000 loci tested at 5% level will have about 5,000 false positives; etc.). In order to keep the cumulative error at or below 5%, the significance level is lowered at each locus/chromosome/position marker. That said, techniques can be employed to account for errors in the GWAS analysis, including the multiple testing error, etc. For example, the computing device 102 may be configured to correct for multiple testing error, through use of the false discovery rate (FDR) correction (or, e.g., Bonferroni correction, etc.), to control for the source of error associated with the number of tests included in the GWAS analysis (e.g., which is generally equal to the number of markers included in the chromosome (e.g., sixty thousand, or more, or less, etc.), etc.).

Thereafter, in particular, the computing device 102 may be configured to render the aggregate data structure as a plot (e.g., a Manhattan plot, etc.), which includes the −log (p-value) on the y-axis by a measure of SNPs (which are physical or genetic locations) along the x-axis. The computing device 102 may then be configured to employ one or more auto-peak detection algorithms to the plot, whereby significant results are defined as peaks that satisfy a defined threshold. The defined threshold may be defined by any suitable standard statistical technique such as, for example, FDR, etc. In the aggregate data structure, the number of peaks detected by the computing device 102 are numerous, and beyond what is identifiable manually. Thus, the computing device 102 is configured to uniquely employ the aggregate data object to combine the signals across the various segment data structures and identify an aggregate set of signals as significant across the segment data structure (which is representative of the macro-environments, etc.).

The output of the auto-peak detection algorithm (generated by the computing device 102) may include the index of the peak maximum, the peak width, and other statistics that describe the peak characteristics, etc. While the peak maximum and the peak width are of interest in certain embodiments, other statistics may include, for example, relative height, threshold, distance, window length (wlen), prominence, plateau size, etc., and may be considered in other embodiments.

It should be appreciated that the example embodiment may further include one or more forms of filtering, including, for example, filtering data potentially subject to high population structure. In particular, population structure should be understood to be a potential source of false positives in the breeding data utilized herein. And, in order to reduce the false positive rate, the aggregate data structure may include, but is not limited to, the following methodologies for controlling population structure, for example, testing the inclusion of multiple principle components for inclusion in the model coupled with automatic selection of the model-of-best-fit, eliminating noise thought to be the result of population structure as a step of the auto-peak detection algorithm, and filtering out/dropping some individual data segments that appear to have very high subpopulation structure from the larger analysis.

In this example embodiment, the outputs from the computing device 102, therefore, may include, but are not limited to, the "peaks" as defined by the peak detection algorithm, statistics indicative of the peaks including, but not limited to, individual SNPs found in those peaks, physical locations of the peaks, genetic location(s) of the peaks, degrees and distributions of p-values of the SNPs in each peak, specific data-subsets that contributed to a given peak reaching the significance threshold, and size/width of the peak, etc. The computing device 102 may further generate any number of suitable plots, whereby the outputs may also include the generated plots including, but not limited to, QQ-plots, boxplots, plots generated by the auto-peak detection, aggregate Manhattan plots, and "Manhattan Blots", as well as any summary data structures including the above statistics, etc. (see, Spindel, J. E., Dahlberg, J., Colgan, M., Hollingsworth, J., Sievert, J., Staggenborg, S. H., Vogel, J. P. (2018) (Association mapping by aerial drone reveals 213 genetic associations for *Sorghum bicolor* biomass traits under drought), Bmc Genomics, 19(1), 679).

In this example embodiment, optionally, the computing device 102 may be configured to join, within the aggregate data structure, the SNPs that are found in the same peak for a further "haplotype test", in which a second p-value is calculated to determine if individual combinations of more than one SNP are also associated with differences in expression of the specific phenotypic characteristic of the implementation (e.g., height, etc.). The computing device 102 is configured to store the results in a manner similar to the results for individual SNPs with the aggregate data structure. It should be appreciated that, through this further configuration, allelic substitution effects may be estimated for both significant individual SNPs and significant haplotypes.

It should be further understood as part of the present disclosure that the results of the individual SNP analysis (as well as the results of the haplotype analysis) may be employed in any number of applications (as described more below), including, but not limited to, searching for gene or allelic effects to include in predictive breeding models (i.e. GWAS+Genomic Selection models), to identify targets for marker assisted breeding programs, to identify targets for gene editing efforts, to guide decision making during the production of transgenic crops, and/or to further biological knowledge underlying traits that are of key agricultural importance. For example, the results of the SNP analysis may be employed to modifying one or more sequences at selected one or more genetic locations in a sequence of a plant type or a species of plant line. And, plant or plant line, having the modified sequence, or part thereof, may be included or planted in a breeding pipeline for use in creating new plants (e.g., for commercial use, as part of one or more breeding programs, etc.). In connection therewith, the plants may be included or planted in growing spaces (e.g., a greenhouse, a nursery, a breeding plot, a field, etc.) of the breeding pipeline and grown (or subsequently derived). That said, in some embodiments, therefore, the system 100 may include such breeding pipeline and/or growing spaces.

Figure 2:
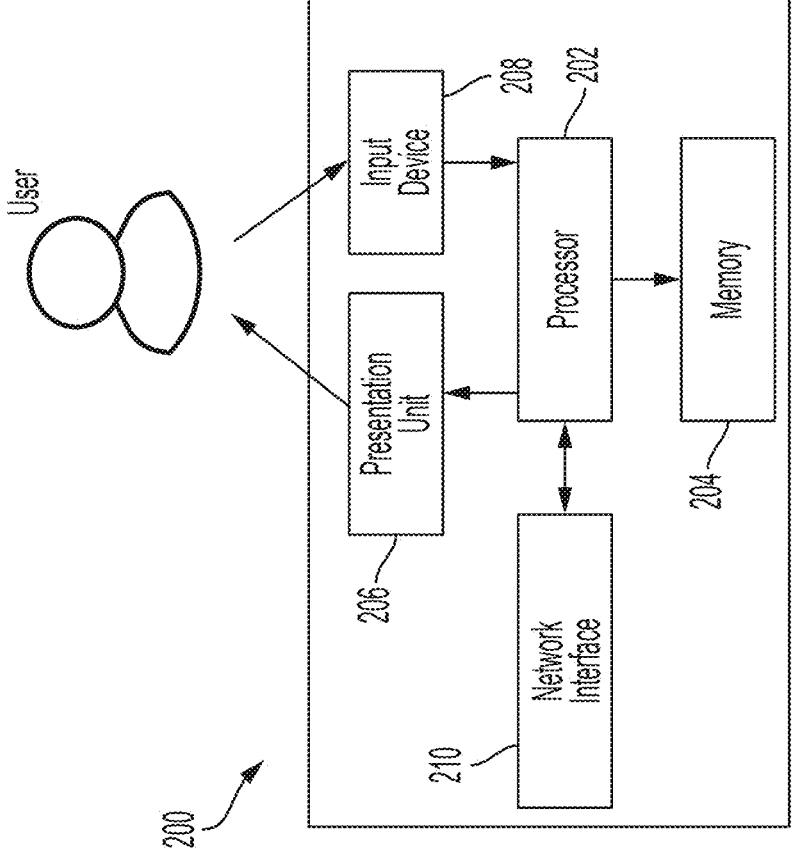
FIG. 2 is a block diagram of a computing device that may be used in the example system of FIG. 1.

FIG. 2 illustrates an example computing device 200 that may be used in the system 100, etc. In connection therewith, the computing device 102 of the system 100 includes one or more computing devices at least partially consistent with computing device 200. The computing device 200 may be configured, by executable instructions, to implement the various algorithms and other operations described herein with regard to the computing device 102. It should be appreciated that the system 100, as described herein, may include a variety of different computing devices, either consistent with computing device 200 or different from computing device 200.

The example computing device 200 may include, for example, one or more servers, workstations, personal computers, laptops, tablets, smartphones, other suitable computing devices, virtual workspaces, combinations thereof, etc. In addition, the computing device 200 may include a single computing device, or it may include multiple computing devices located in close proximity or distributed over a geographic region, and coupled to one another via one or more networks. Such networks may include, without limitations, the Internet, an intranet, a private or public local area network (LAN), wide area network (WAN), mobile network, telecommunication networks, combinations thereof, or other suitable network(s), etc. In one example, the computing device 102 and/or the databases 104, 106, 108, and 110 may include and/or may be implemented in at least one computing device consistent with the computing device 200. In addition, the databases 104, 106, 108, and/or 110 of the system 100 each include at least one server computing device, while the computing device 102 includes at least one separate computing device, which is coupled to the databases 104, 106, 108, and/or 110, directly and/or by one or more LANs, etc.

With that said, the illustrated computing device 200 includes a processor 202 and a memory 204 that is coupled to (and in communication with) the processor 202. The processor 202 may include, without limitation, one or more processing units (e.g., in a multi-core configuration, etc.), including a central processing unit (CPU), a microcontroller, a reduced instruction set computer (RISC) processor, an application specific integrated circuit (ASIC), a programmable logic device (PLD), a gate array, and/or any other circuit or processor capable of the functions described herein. The above listing is example only, and thus is not intended to limit in any way the definition and/or meaning of processor.

The memory 204, as described herein, is one or more devices that enable information, such as executable instructions and/or other data, to be stored and retrieved. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, tapes, hard disks, and/or any other type of volatile or nonvolatile physical or tangible computer-readable media. The memory 204 may be configured to store, without limitation, phenotypic data, genotypic data (e.g., SNPs, etc.), probability values, line identifiers, p-values, peak characteristics, linear models, other models, and/or other types of data (and/or data structures) suitable for use as described herein, etc. In various embodiments, computer-executable instructions may be stored in the memory 204 for execution by the processor 202 to cause the processor 202 to perform one or more of the functions described herein, such that the memory 204 is a physical, tangible, and non-transitory computer-readable storage media. It should be appreciated that the memory 204 may include a variety of different memories, each implemented in one or more of the functions or processes described herein.

Furthermore, in various embodiments, computer-executable instructions may be stored in the memory 204 for execution by the processor 202 to cause the processor 202 to perform one or more of the functions described herein (e.g., one or more of the operations of method 300, etc.), such that the memory 204 is a physical, tangible, and non-transitory computer readable storage media. Such instructions often improve the efficiencies and/or performance of the processor 202 that is performing one or more of the various operations herein (e.g., the performance of the computing device 200, etc.), whereby in connection with such performance the computing device 200 may be transformed into a special purpose computing device. It should be appreciated that the memory 204 may include a variety of different memories, each implemented in one or more of the functions or processes described herein.

In the example embodiment, the computing device 200 also includes a presentation unit 206 that is coupled to (and is in communication with) the processor 202. The presentation unit 206 outputs, or presents, to a user of the computing device 200 (e.g., a breeder, etc.) by, for example, displaying and/or otherwise outputting information such as, but not limited to, peak descriptions, plots, probability values, etc. It should be further appreciated that, in some embodiments, the presentation unit 206 may comprise a display device such that various interfaces (e.g., applications (network-based or otherwise), etc.) may be displayed at computing device 200, and in particular at the display device, to display such information and data, etc. And in some examples, the computing device 200 may cause the interfaces to be displayed at a display device of another computing device, including, for example, a server hosting a website having multiple webpages, or interacting with a web application employed at the other computing device, etc. Presentation unit 206 may include, without limitation, a liquid crystal display (LCD), a light-emitting diode (LED)

display, an organic LED (OLED) display, an "electronic ink" display, combinations thereof, etc. In some embodiments, presentation unit 206 may include multiple units.

The computing device 200 further includes an input device 208 that receives input from the user. The input device 208 is coupled to (and is in communication with) the processor 202 and may include, for example, a keyboard, a pointing device, a mouse, a touch sensitive panel (e.g., a touch pad or a touch screen, etc.), another computing device, and/or an audio input device. Further, in some example embodiments, a touch screen, such as that included in a tablet or similar device, may perform as both presentation unit 206 and input device 208. In at least one example embodiment, the presentation unit 206 and input device 208 may be omitted.

In addition, the illustrated computing device 200 includes a network interface 210 coupled to (and in communication with) the processor 202 (and, in some embodiments, to the memory 204 as well). The network interface 210 may include, without limitation, a wired network adapter, a wireless network adapter, a telecommunications adapter, or other device capable of communicating to one or more different networks. In at least one embodiment, the network interface 210 is employed to receive inputs to the computing device 200. For example, the network interface 210 may be coupled to (and in communication with) in-field data collection devices, in order to collect data for use as described herein. In some example embodiments, the computing device 200 may include the processor 202 and one or more network interfaces incorporated into or with the processor 202.

Figure 3:
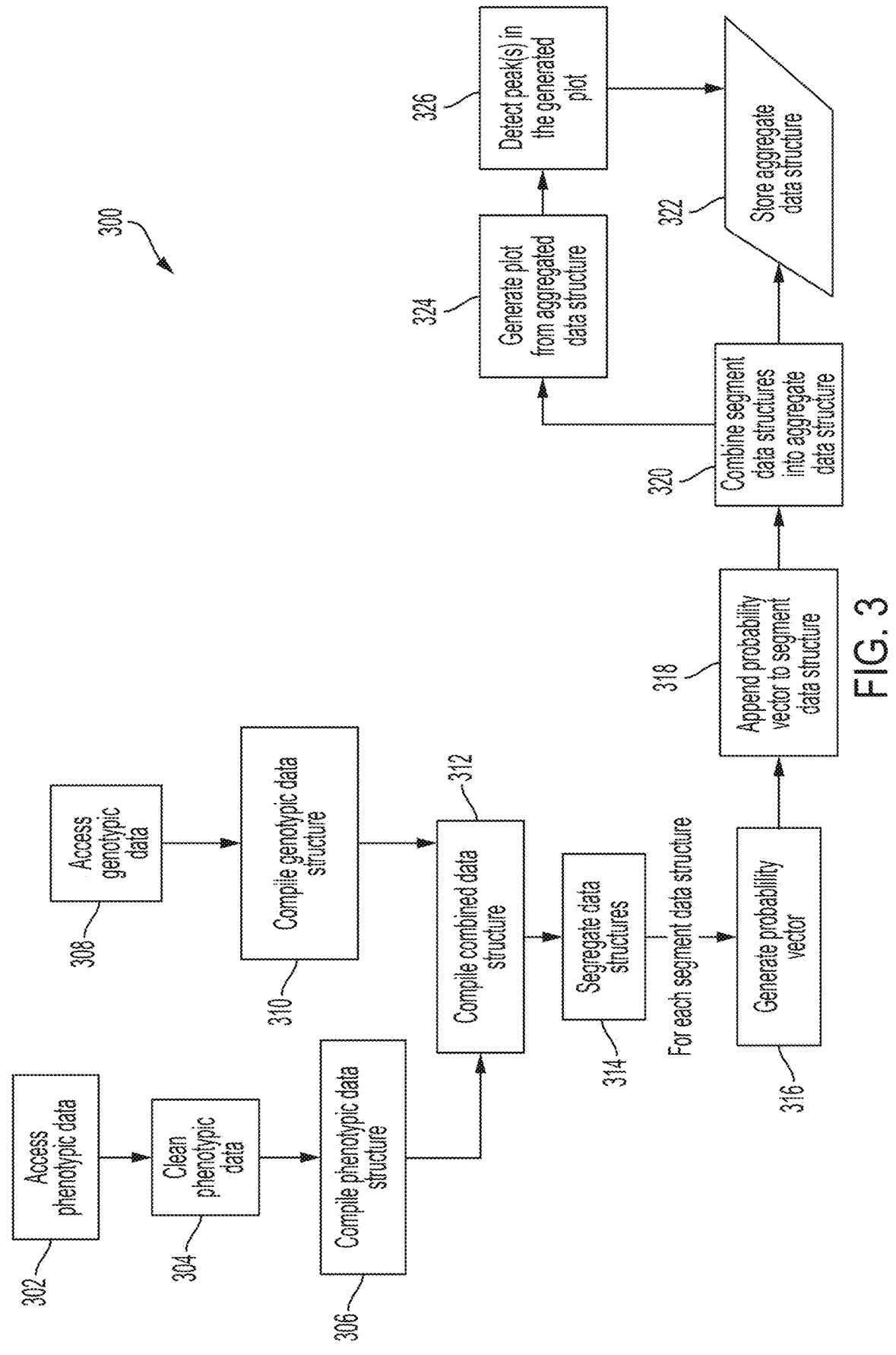
FIG. 3 is an example method, suitable for use with the system of FIG. 1, for linking phenotypic data from a crop to genotypic data for the crop, through probability values and through segregation of the data based on one or more factors.

FIG. 3 illustrates an example method 300 of linking phenotypic data from a crop to genotypic locations, by probability values, based on segregation of the data based on one or more factors. The example method 300 is described herein in connection with the system 100, and may be implemented, in whole or in part, in the computing device 102 of the system 100. Further, for purposes of illustration, the example method 300 is also described with reference to the computing device 200 of FIG. 2. However, it should be appreciated that the method 300, or other methods described herein, are not limited to the system 100 or the computing device 200. And, conversely, the systems, data structures, and the computing devices described herein are not limited to the example method 300.

Initially, a breeder (or other user) identifies a crop (e.g., corn, soybeans, etc.) and a phenotypic characteristic to be investigated, potentially consistent with one or more desired characteristics and/or traits to be advanced in the identified plant type, or a desired performance in a commercial plant product. Additionally, or alternatively, the user may be interested in compiling reference material for various phenotypes of interest (e.g., one at a time through method 300, etc.), which may be consulted and/or employed, in one form or another in various implementations, etc. In turn, based on the above and/or one or more other criteria, the user, alone or through various processes, identifies to the computing device 102 the selected species (broadly, plant type) (e.g., corn hybrid, corn inbred, canola, soybean, etc.) and the selected phenotype (i.e., a target phenotype) for which to perform the method 300. For purposes of illustration, the selected species in the description of the method 300 is inbred corn, and the target phenotype is stalk height.

As shown in FIG. 3, in response, the computing device 102 accesses, at 302, the phenotypic data from the database 104, and in particular, phenotypic data for the selected plant type. Again, in this example, the selected plant type is inbred corn, whereby the phenotypic data is specific to inbred corn. The accessed data may include hundreds, thousands, or tens of thousands, or more or less, of lines of inbred corn entries (e.g., for each different line, season, and/or location, etc., or duplicates thereof; etc.) for lines of inbred corn over a number of years in one or more different locations. For example, one entry may include a plant ID of 12345678 for the inbred corn line, a planting season of 2018, a field identifier 123ABCD for the field (e.g., a proxy for location, etc.), stalk height for the line, ear height, yield, stalk strength, kernel row number, node injury, test weight, etc., or other suitable phenotypic data, identification data, or location data, as described, for example, with reference to Table 1.

The computing device 102 then imposes quality controls, at 304, on the phenotypic data (e.g., cleans the phenotypic data, etc.). In particular, for example, the computing device 102 may convert all units, for each specific phenotype, to a common unit (e.g., meters, inches, centimeters, grams, ounces, etc.). The computing device 102 may further analyze the phenotypic data, for example, to identify outliers, and remove the outliers. Such analysis may be performed through one or more statistical techniques, etc. In addition, the computing device 102 may perform other techniques to ensure and/or improve the phenotypic data received/retrieved from the database 104, for example (e.g., to account for human errors, differences in type of data collection or data collected, differences among regions associated with the collected data, etc.). It should be appreciated that imposing such controls on (e.g., the cleaning of, etc.) the phenotypic data may be omitted in certain embodiments, as such controls may be considered dependent, generally, on condition of data (actual or preserved) included in the database 104, for example.

Thereafter, at 306, the computing device 102 compiles the phenotypic data into a phenotypic data structure (e.g., as an object, etc.). The data structure (or object) may be stored locally in memory of the computing device 102 (e.g., the memory 204, etc.), or in associated computing devices local with the computing device 102, or in cloud storage offered by one or more service providers. In general, location of and/or access to the data may be affected and/or dictated by the amount of data accessed and/or compiled in the data structure (or object) and/or the manner of accessing the data structure.

Subsequently, or otherwise, the computing device 102 accesses, at 308, the genotypic data from the database 106, and in particular, genotypic data for the selected plant type. Again, in this example, the plant type is corn, whereby the genotypic data is specific to inbred corn and includes, for example, the sequences of available inbred corn plants. The sequences generally include SNPs, which define specific genetic locations within the inbred corn plant. It should be appreciated that one or more quality controls (e.g., cleaning techniques, etc.) may be optionally imposed or employed, by the computing device 102, for the genotypic data as needed and/or desired (in a generally similar manner to the controls described with regard to the phenotypic data). Thereafter, at 310, the computing device 102 compiles the genotypic data into a genotypic data structure (e.g., as an object, etc.). Again, the genetic data structure may be stored in local memory of the computing device 102 (e.g., the memory 204, etc.), or otherwise, as described herein.

The computing device 102 then compiles the phenotypic data structure and the genotypic data structure, or parts thereof, into a combined data structure, at 312. The data structures are combined based on data include therein, such as, for example, a plant ID, a germplasm ID, or other data included in the data structures or otherwise known to the computing device 102 (e.g., that is consistent or unique across the data structures, etc.), etc.

Then, in connection with a GWAS, the computing device 102 separates or sub-sets, at 314, the combined data structure into multiple segment data structures, where each of the multiple segment data structures includes phenotypic and genetic data. The computing device 102 may sub-set the data based on one or more factors associated with similarities of the selected plant, plant type, location, date, etc., underlying the data. For example, all plant types of the same year, or season, may be sub-setted together. In addition, or alternatively, plant types from the same region and/or subjected to one or more treatments may be sub-setted together. In the example method 300, the computing device 102 separates (or sub-sets) the data based on, at least, location and timing (e.g., per year, etc.). Factors used in separating the combined data may be based on similarity of the plant types underlying the data, and also based on the data included in the resulting data structures (e.g., a minimum data, etc.). It should be appreciated that, for example, combined data structures may be segregated into 12, 50, 100, or more or less segment data structures, etc. For example, where the combined data structure is sub-setted into 50 different macro-environments in the segment data structures (e.g., per year and per field divisions, etc.), the data may include 60,000 SNPs in each of the segment data structures along with the phenotypic data for the inbred corn plant of the particular year, in the particular location of the macro-environment.

It should be appreciated that the association or linking in the embodiment of method 300 is directed to a single variable, or single phenotype. As such, in combining the data into the combined data structure, or into the segment data structures, the computing device 102 may omit irrelevant data. For example, where the single variable is ear count per stalk, the computing device 102 may omit or leave behind data unrelated to ear count (and unused in the steps below). For example, the combined data structure may include line IDs, stalk strength, height, ear count per stalk, location, growing year and genotypic data, while the segment data structures may each include only ear count per stalk, growing year, location, line IDs, and genotypic data. It should be appreciated that the data included in the different segment data structures may be altered to account for processing and/or memory limitations and/or efficiencies, etc. What's more, where the phenotypic data includes multiple entries for the same plant types within the combined data structure, the computing device 102 may average or otherwise combine the phenotypic data for the specific plant type to consolidate the plant type to a single entry in each of the segment data structures.

Next, at 316, the computing device 102 generates, for each segment data structure, a probability vector for the plant type, which includes a probability value for each marker (broadly, division) of the sequence of the plant type (e.g., SNP, etc.). The probability vector is generated, for the GWAS, via a linear model, such as, for example, GEMMA or other suitable model (e.g., multivariate models, nonlinear models, and/or linear or non-linear models, etc.), as indicated above. In particular, for GEMMA, the computing device 102 employs numerous variables, including, for example, the genotype data, phenotype data, and covariate data structures, as well as the selected linear modeling options.

When complete, the computing device 102 appends, at 318, the probability vector (from the model) to each segment data structure, for example, as a new column or series of columns in the data structure, etc. The segment data structures are then combined, at 320, (with one another or) back into the combined data structure to provide an aggregate data structure. It should be appreciated that the aggregate data structure may include as much or as little data from the combined data structure as desired and/or needed, depending, for example, on intended uses of the aggregate data structure. In this example, the probability values or p-values are concatenated with one another into the aggregate data structure, for each of the SNPs. It should be understood that the example embodiment of FIG. 3 includes, for example, thousands, or tens of thousands (or more or less) of inbred corn lines in the aggregate data structure. Consequently, the number of lines considered, and included in the aggregate data structure, impacts the power of the overall determination of method 300. It should be appreciated that the segment data structure, for each macro-environment, may also be preserved separately (in addition to the aggregate data structure).

And, further in method 300, the aggregate data structure (and potentially, the separate segments data structures) is stored, at 322, in memory, either locally with the computing device 102 (e.g., the memory 204 of the computing device 102, etc.), remotely, or in physical storage or in cloud-based storage (broadly, in memory 204).

Figure 4:
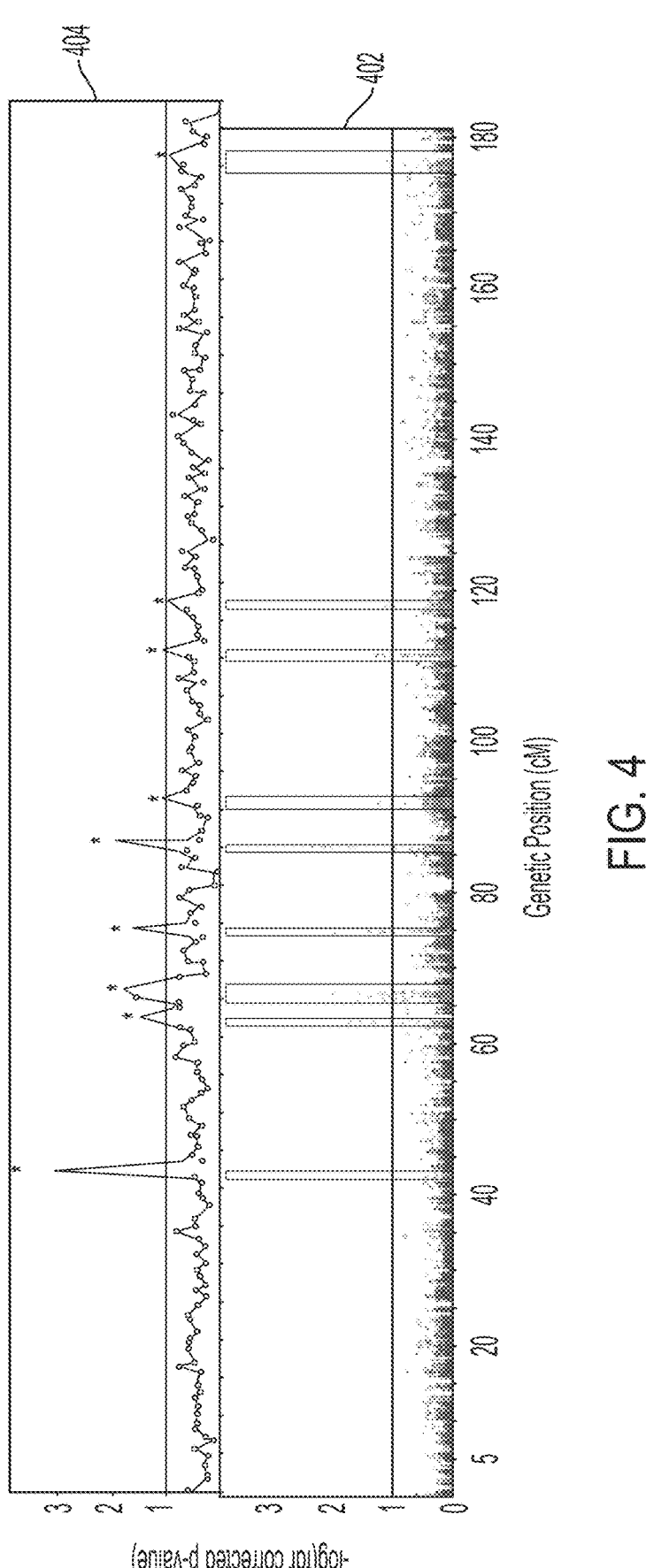
FIG. 4 illustrates an example graphical representation of p-values across genetic locations of a chromosome, which may be output from the method of FIG. 3.

Next, the computing device 102 generates, at 324, one or more plots of the aggregate data structure, and in particular, the p-values per SNP. In this example embodiment, the computing device 102 generates a Manhattan plot, with the x-axis being the genetic position of the SNP and the y-axis being the −log of the p-value across all individual data segments. FIG. 4 (lower, 402), for example, illustrates an aggregate Manhattan plot for a specific chromosome (e.g., for maize, there are ten (whereby there would be ten plots per plant line); etc.), where p-values across the sub-experiments are plotted on the y-axis by position on the x-axis (e.g., as associated with the threshold, etc.). The computing device 102 then performs peak detection, at 326, as shown on FIG. 4 (upper, 404) based on a filtered subset of the p-values. This identifies the peaks of the plot which exceed a threshold. The threshold may be based on, for example, any suitable statistical technique, including, for example, false discovery rate (FDR), etc. The peak detection output is provided at the upper portion 404 of the diagram of FIG. 4.

The detected peak(s) at corresponding SNP(s) (broadly, results or output of the method 300) are then stored in the output database 110 (along with or apart from the aggregate data structure (or other data structures described above)) and may be employed in a variety of different applications, including, for example, gene editing, transgene insertion, trait integration, breeding selection, etc.

Figure 5:
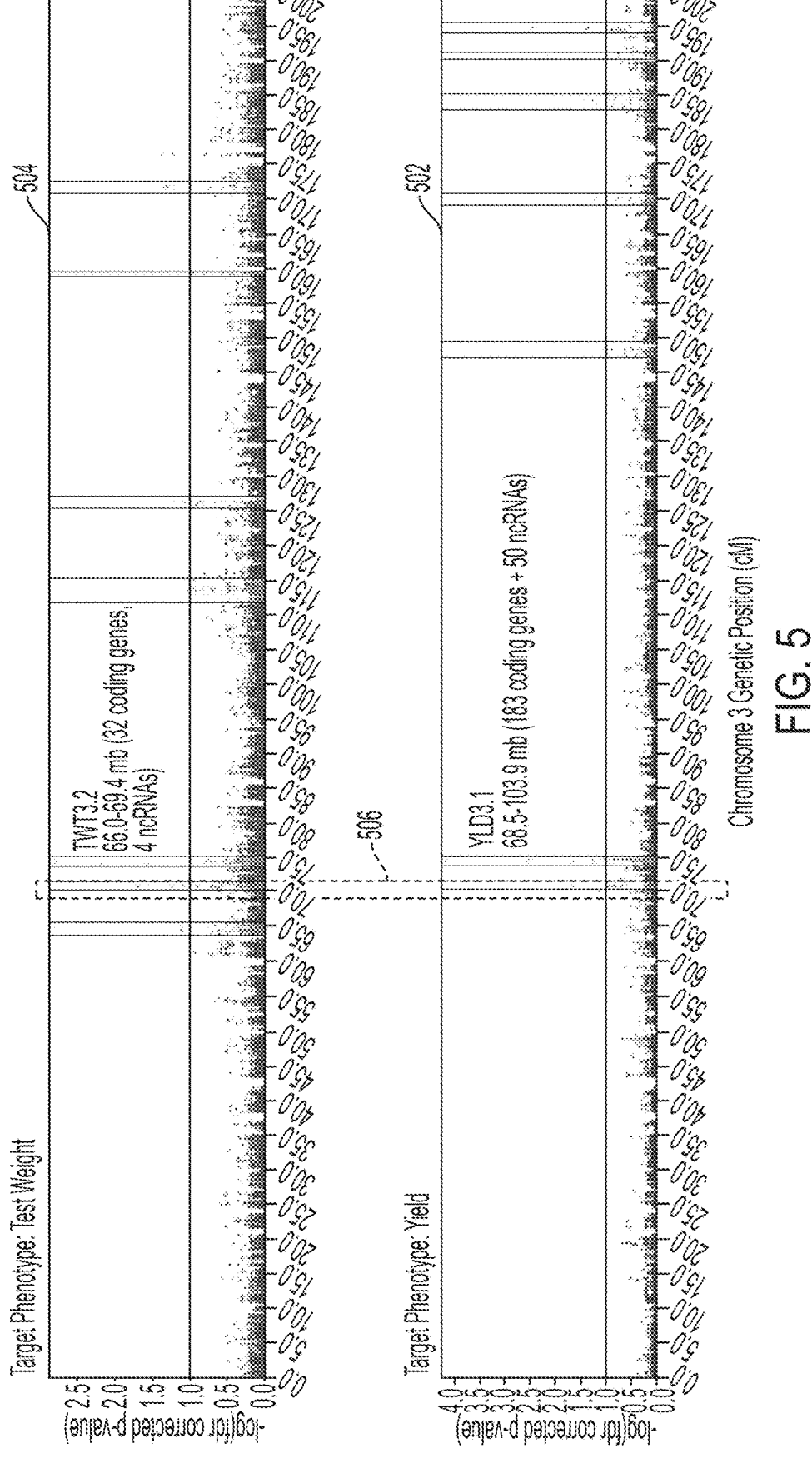
FIG. 5 illustrates an example graphical representation of multiple plots associated with a single target phenotype of a maize crop with peak detection, which may be provided in one implementation of the method of FIG. 3.

In one example, the results may be employed to identify a locus that can be edited to produce one or more new and beneficial genetic variation(s) that can then be selected to improve a crop. In particular, metrics such as the size of the peak, the number of sub-experiments that resulted in the peak, the estimated phenotypic effect size, and genic regions/non-genic regions where markers can be anchored to the reference genome, can be employed to identify a locus for editing. For example, FIG. 5 shows an example of a region that can be targeted for inducing genetic variation by gene editing. The same peak is identified for both a plot 502 where yield is the target phenotype and a plot 504 where test weight is the target phenotype. It should be appreciated that the region 506 is relatively narrow, which provides a narrow region to target for editing. A locus identified as described herein may be targeted by a sequence-specific editing system to induce genetic variation within the locus without first identifying genes within the locus.

In another example, the results may be employed to identify genes that can be edited to produce new and beneficial variants to improve a crop. In particular, the metrics included in Table 3 may be useful: the size of the peak (e.g., smaller is easier to identify candidates, etc.), the number of sub-experiments that resulted in the peak (e.g., more is better, etc.), the estimated phenotypic effect size (e.g., larger is better, etc.), and genic regions/non-genic regions where markers can be anchored to the reference genome. Table 3 shows an example of the data for identifying targets for gene editing. And, FIG. 5 shows an example of a region that is targeted for candidate gene identification. The same peak is identified for both a plot 502 where yield is the target phenotype and a plot 504 where test weight is the target phenotype. It should be appreciated that the region 506 is relatively narrow with many coding genes, which provides a good region in which to identify gene candidates for editing.

In another example, transgenes may be introduced into a genetic location that is linked to a location that is identified as described herein and that contains important breeding haplotypes. By analyzing the results, a location for transgene insertion can be selected that is linked to a genetic location where many or large effect peaks have been detected. As used herein, the term "linkage" or "linked" refers a phenomenon wherein loci or genes on the same chromosome tend to segregate together more often than expected by chance if their transmission was independent.

In another example, the results may be employed to identify a first locus and a second locus and enhancing recombination between the identified genomic loci, by providing at least one sequence-specific editing system that induces recombination between the first locus and the second locus.

In a further example, the results are implemented in combination with genome-wide selection (GWS) in order to predict the breeding values of progeny in a breeding program (see, J. E. Spindel et al., 2016 herein). Specifically, by incorporating the results (e.g., peaks and genic locations,

TABLE 3

| Peak name | p grand min | p grand max | p grand median | Min effect | Mean effect | Max effect | EXPs count | Years count | RMs count |
|---|---|---|---|---|---|---|---|---|---|
| 1.0 | 0.8 | 1.0 | 1.2 | −2.4 | 5.4 | 13.4 | 2 | 2 | 2 |
| 1.1 | 0.8 | 1.6 | 4.3 | −26.1 | −6.1 | 11.8 | 4 | 3 | 3 |
| 1.2 | 0.8 | 1.5 | 3.2 | −22.6 | −0.95 | 9.6 | 5 | 4 | 4 |

| chr | cM start pos | cM end pos | bp start | Bp end | cM length | Phys length Kbp | nsnps | Total GA count |
|---|---|---|---|---|---|---|---|---|
| 1 | 108.1 | 108.4 | 144756363 | 149533512 | 0.3 | 4777.149 | 2 | 1641 |
| 1 | 138.7 | 140.0 | 202508757 | 204321307 | 1.3 | 1812.55 | 7 | 2366 |

In another example for introducing a new transgene into breeding germplasm, during trait integration, multiple events may be generated and eventually narrowed down to a single event that will be introduced widely by breeding into different germplasms. Events are specific to a particular genetic location, and deleterious effects on germplasm performance can occur if the event is in a location that contains important breeding haplotypes. By analyzing the results, events may be omitted or eliminated when the events are likely to cause such deleterious results by avoiding loci where many or large effect peaks have been detected, as illustrated in Table 4. In Table 4, specific event identifiers are provided along with the number of peaks within 2 cM of the event (i.e., centimorgan) (although it should be appreciated that the peaks may also be defined by m.u. or map unit, as distance between comparison positions (or loci/markers)). Code (G) for green events are prioritized; code (Y) for yellow are "use with caution"; and code (R) for red are "do not use".

etc.) into selection models, accuracy of the model can be improved, thus resulting in increased genetic gain per unit time. What's more, the metrics associated with the results (e.g., as included in Table 3, etc.) are used to determine how to incorporate peak detection results into a selection model, including, but not necessarily limited to, the estimated effect of phenotype, the number and distribution of sub-experiments that resulted in the peak, and the peak p-value, etc.

In some examples, the results of the above may be implemented in a breeding pipeline. In connection therewith, plants or plant lines having one or more desired modified sequence(s) (as defined above) may be included in breeding pipelines for use in creating new plants (e.g., for commercial use, as part of one or more breeding programs, etc.). In doing so, the plants may be included or planted in growing spaces (e.g., greenhouses, nurseries, breeding plots, fields, etc.) of the breeding pipelines and grown (or subsequently derived).

In view of the above, the systems and methods herein provide for prediction of genetic location(s) impacting a target phenotype. In particular, the systems and methods herein provide for the ingestion of significant data across various sequences of plant types or species, whereby upwards of dozens or hundreds of peaks, per trait, are able to be recognized by the processing of the data consistent with the description herein. The prediction provides not only for the consideration of volumes of data, but also provides improved validation of the causation between the genetic location(s) and the target phenotypes over conventional methods.

TABLE 4

| Event identifier | Code | # peaks for 25 traits within 2 cM of event |
|---|---|---|
| ZM1 | (G) | 2 |
| ZM2 | (Y) | 6 |
| ZM3 | (Y) | 7 |
| ZM4 | (Y) | 8 |
| ZM5 | (R) | 12 |
| ZM6 | (R) | 13 |
| ZM7 | (R) | 16 |

With that said, it should be appreciated that the functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques, including computer software, firmware, hardware or any combination or subset thereof, wherein the technical effect may be achieved by performing at least one of the following operations: (a) accessing a phenotypic database and compiling, by a computing device, a phenotypic data structure including phenotypic data from multiple different plant lines in the phenotypic database, each of the different plant lines consistent with a single plant type or species; (b) accessing a genotypic database and compiling, by the computing device, a genotypic data structure including genotypic data for multiple different plant lines in the genotypic database, the genotypic data including a sequence for each of the multiple plant lines; (c) combining, by the computing device, the phenotypic data structure and the genotypic data structure into a combined data structure based on an identifier included in each of the phenotypic data structure and the genotypic data structure; (d) separating, by the computing device, the combined data structure into multiple segment data structures, based on one or more factors, each segment data structure including at least data for a target phenotype and genotypic data for each of the multiple plants; (e) for each of the multiple segment data structures, generating, by the computing device, a probability vector based on a linear model, the probability vector including a probability value for each of multiple genetic locations in the sequence of the plant species; (f) appending, by the computing device, each probability vector for the target phenotype to the respective segment data structure; and (g) combining the multiple segment data structures into an aggregate data structure, the aggregate data structure including at least a portion of the phenotypic data for the plant species, the genotypic data and/or the probability vectors for the plant species, whereby the target phenotype is linked, by the probability vector, to one or more of multiple divisions of the sequence.

Examples and embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more example embodiments disclosed herein may provide all or none of the above mentioned advantages and improvements and still fall within the scope of the present disclosure.

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may also be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

An editing system useful to modify a locus identified as described herein can be any sequence-specific editing system now known or later developed, which system can modify DNA in target specific manner.

For example, a sequence-specific editing system can include, but is not limited to, an RNA-guided nuclease editing system, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Cas 12a (also known as Cpf1), Csy1, Csy2, Csy3, Cse1, Csc2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, CasY, Mad7) and CRISPR array (CRISPR guide) nucleic acid that when expressed or introduced as a system in a cell can modify a target nucleic acid in a sequence specific manner. Other examples of sequence-specific editing systems include a meganuclease editing system, a zinc finger nuclease (ZFN) editing system, a transcription activator-like effector nuclease (TALEN) editing system. In some embodiments, a sequence-specific editing system can comprise one or more sequence-specific nucleic acid binding domains (DNA binding domains) that can be from, for example, a polynucleotide-guided effector protein (e.g., a Cas9, a Cas12a), a zinc finger protein, and/or a transcription activator-like effector protein (TALE) and an effector domain that modifies the DNA. Examples of effector domains include cleavage domains (e.g., nucleases) including, but not limited to, an endonuclease (e.g., Fok1), a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but not limited to, an extended guide nucleic acid, and/or a reverse transcriptase template. In some embodiments, a sequence-specific editing system can comprise one or more polynucleotides and/or one or more polypeptides, including but not limited to a nucleic acid binding domain (DNA binding domain), a nuclease, and/or other polypeptide, and/or a polynucleotide.

In some embodiments, a method of modifying a genetic locus and/or gene identified as described herein may comprise contacting the targeted nucleic acid with a base-editing fusion protein (e.g., a sequence-specific DNA binding protein (e.g., a CRISPR-Cas9 effector protein or domain, a CRISPR-Cas12a effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing the identified genetic locus. In some embodiments, the nuclease activity of the sequence-specific DNA binding protein (e.g., a CRISPR-Cas9 effector protein or domain, a CRISPR-Cas12a effector protein or domain has been inactivated. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, modifying a genetic locus or gene identified as described herein may comprise contacting a target nucleic acid with a sequence-specific editing system (e.g., a CRISPR-Cas9 editing system, a CRISPR-Cas12a editing system, a meganuclease editing system, a zinc finger nuclease (ZFN) editing system, a transcription activator-like effector nuclease (TALEN) editing system, that induces cleavage of one or both strands of the target nucleic acid thereby modifying the identified genetic locus or gene. In some embodiments, a sequence-specific editing system may be comprised in one or more expression cassettes. In some embodiments, the sequence-specific editing system may be provided as ribonucleoproteins (RNPs). In some embodiments, the target nucleic acid may be contacted with a sequence-specific editing system (e.g., a CRISPR-Cas9 editing system, a CRISPR-Cas12a editing system) comprising a guide nucleic acid that comprises a sequence which is complementary to the target nucleic acid. In some embodiments, a cell may be contacted with more than one sequence-specific editing systems that may target one or more target nucleic acids in the cell. In some embodiments, a cell may be contacted with one or more sequence-specific editing system (e.g., a CRISPR-Cas9 editing system, a CRISPR-Cas12a editing system) comprising one or more guide nucleic acids that may target one or more target nucleic acids in the cell.

As used herein, the term "sequence-specific editing system" refers to any enzyme or nucleo-protein complex that can modify a nucleotide sequence in a sequence-specific manner. In some embodiments, a sequence-specific editing system modifies the a genetic locus or gene identified as described herein by inducing a single-strand break. In some embodiments, a sequence-specific editing system modifies a genetic locus or gene identified as described herein by inducing a double-strand break. In some embodiments, a sequence-specific editing system comprises a cytidine deaminase. In an aspect, a "modification" comprises the hydrolytic deamination of cytidine or deoxycytidine to uridine or deoxyuridine, respectively. In some embodiments, a sequence-specific editing system comprises an adenine deaminase. In an aspect, a "modification" comprises the hydrolytic deamination of adenine or adenosine. In an aspect, a "modification" comprises the hydrolytic deamination of adenosine or deoxyadenosine to inosine or deoxyinosine, respectively. In an aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C", "G" or "T" in a nucleic acid sequence. In some embodiments, a "modification" comprises the substitution of a "C" for an "A", "G" or "T" in a nucleic acid sequence. In some embodiments, a "modification" comprises the substitution of a "G" for an "A", "C" or "T" in a nucleic acid sequence. In some embodiments, a "modification" comprises the substitution of a "T" for an "A", "C" or "G" in a nucleic acid sequence. In some embodiments, a "modification" comprises the substitution of a "C" for a "U" in a nucleic acid sequence. In some embodiments, a "modification" comprises the substitution of a "G" for a "A" in a nucleic acid sequence. In some embodiments, a "modification" comprises the substitution of an "A" for a "G" in a nucleic acid sequence. In some embodiments, a "modification" comprises the substitution of a "T" for a "C" in a nucleic acid sequence. In some embodiments, a "modification" comprises the insertion of one or more transgenes.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for linking phenotypic data with genotypic data for plants, in connection with facilitating plant development, the method comprising:

accessing a phenotypic database and compiling, by a computing device, a phenotypic data structure including phenotypic data for multiple different plant lines represented in the phenotypic database, each of the multiple different plant lines consistent with a single plant type or species;

accessing a genotypic database and compiling, by the computing device, a genotypic data structure including genotypic data for the multiple different plant lines represented in the genotypic database, the genotypic data including a sequence for each of the multiple different plant lines;

combining, by the computing device, the phenotypic data structure and the genotypic data structure into a combined data structure, based on at least an identifier included in each of the phenotypic data structure and the genotypic data structure;

separating, by the computing device, the combined data structure into multiple segment data structures, based on one or more factors, each segment data structure including at least data for a target phenotype and genotypic data for each of the multiple different plant lines;

for each of the multiple segment data structures, generating, by the computing device, a probability vector based on a linear model, the probability vector including a probability value for the target phenotype for each of multiple genetic locations in the sequence of the plant type or species of the plant lines;

appending, by the computing device, each of the generated probability vectors for the target phenotype to the respective segment data structure;

combining the multiple segment data structures into an aggregate data structure, the aggregate data structure including at least a portion of the phenotypic data for the plant type or species, the genotypic data, and the probability vectors for the plant type or species, the probability values being concatenated in the aggregate data structure and sorted by the multiple genetic locations, whereby the target phenotype is linked, by the probability vectors, to one or more of multiple divisions of the sequence;

selecting one of the multiple genetic locations in the sequence of the plant type or species of the plant lines, based on the probability vectors; and modifying the sequence, or a part thereof, at the selected one of the multiple genetic locations of the sequence.

2. The computer-implemented method of claim 1, wherein the combined data structures include phenotypic data for the target phenotype, location, time, and sequence.

3. The computer-implemented method of claim 1, further comprising:

generating, by the computing device, a plot of the provability vectors relative to the genetic locations for the probability vectors;

detecting, by the computing device, in the generated plot, at least one peak; and outputting data indicative of the at least one peak.

4. The computer-implemented method of claim 3, further comprising selecting the modified sequence for inclusion in a breeding pipeline.

5. The computer-implemented method of claim 4, wherein selecting the one of the multiple genetic locations in the sequence of the plant type or species of the plant lines is based on one or more of: a size of the at least one peak, a number of sub-experiments that resulted in the at least one peak, an estimated phenotypic effect size, and/or at least one genic region and/or non-genic region at which markers are anchored to a reference genome; and/or wherein selecting the one of the multiple genetic locations in the sequence of the plant type or species of the plant lines is based on one of more events relative to the at least one peak.

6. The computer-implemented method of claim 4, wherein selecting the one of the multiple genetic locations in the sequence is based on a number and/or size of the at least one peak; and wherein the modified sequence includes a transgene insertion.

7. The computer-implemented method of claim 4, wherein the breeding pipeline includes a growing space; and further comprising planting and/or including a plant derived from the modified sequence in the growing space.

8. The computer-implemented method of claim 1, wherein the multiple divisions of the sequence of the plant type or species include multiple single-nucleotide polymorphisms (SNPs) of the sequence; and wherein the probability vectors include the probability value for each of the multiple SNPs.

9. The computer-implemented method of claim 1, further comprising cleaning, by the computing device, the phenotypic data from the phenotypic database, prior to compiling the phenotypic data structure.

10. The computer-implemented method of claim 1, wherein the linear model includes a linear mixed model.

11. The computer-implemented method of claim 1, wherein the plant lines include one of hybrid corn and inbred corn.

12. The computer-implemented method of claim 1, further comprising storing the aggregate data structure in an output database.

13. The computer-implemented method of claim 1, wherein selecting one of the multiple genetic locations in the sequence of the plant type or species of the plant lines is further based on one or more metric.

14. The computer-implemented method of claim 13, further comprising selecting the modified sequence for inclusion in a breeding pipeline based on at least one peak detected in a plot of the probability vectors relative to the genetic locations for the probability vectors.

15. The computer-implemented method of claim 1, wherein each of the multiple segment data structures includes only the data for the target phenotype and the sequence of the plant type or species separated into the segment data structure.

16. The computer-implemented method of claim 1, wherein combining the phenotypic data structure and the genotypic data structure into a combined data structure includes combining the phenotypic data structure, the genotypic data structure, and a covariate data structure into the combined data structure.

\*    \*    \*    \*    \*